United States Patent [19]

Yun et al.

[11] Patent Number: 5,650,456
[45] Date of Patent: Jul. 22, 1997

[54] COUMARIN DERIVATIVES, A METHOD OF PREPARING THEM AND THEIR USE AS INTERMEDIATES

[75] Inventors: Chen Yun; Rolf Wehrmann, both of Krefeld; Burkhard Köhler, Leverkusen, all of Germany

[73] Assignee: Bayer Aktiengesellschaft, Leverkusen, Germany

[21] Appl. No.: 599,299

[22] Filed: Feb. 9, 1996

[30] Foreign Application Priority Data

Feb. 21, 1995 [DE] Germany .................. 195 05 940.9

[51] Int. Cl.[6] .................. C08K 5/15; C07D 311/02
[52] U.S. Cl. .................. 524/110; 524/96; 524/99; 524/100; 524/104; 544/151; 544/376; 546/196; 548/525; 549/287
[58] Field of Search .................. 549/287; 546/196; 548/525; 544/151, 376; 524/96, 99, 100, 104, 110

[56] References Cited

U.S. PATENT DOCUMENTS 5,286,803  2/1994  Lindsay et al. .................. 525/329.7

FOREIGN PATENT DOCUMENTS 532798  3/1993  European Pat. Off. .
564224  10/1993  European Pat. Off. .

OTHER PUBLICATIONS

Hi, H et al CA111:164206 (1989).
Appl. Phys. Lett. 57:531 (1990).
Pat. Abstr. Japan, JP 4300991 (1992).
Chem. Abstr. 120:310930u (1994).
Pat. Abstr. Japan, JP 63023901 (1988).

*Primary Examiner*—Amelia Owens
*Attorney, Agent, or Firm*—Connolly and Hutz

[57] ABSTRACT

This invention relates to coumarin derivatives of formula (I)

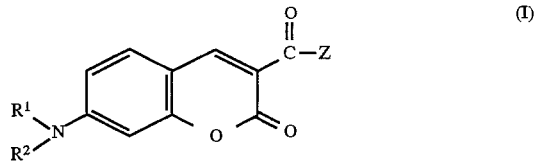

where
  Z represents $OR^3$ or $NR^4R^5$,
to their preparation, and to their use for the production of polymers with luminophors on their side chains.

12 Claims, No Drawings

COUMARIN DERIVATIVES, A METHOD OF PREPARING THEM AND THEIR USE AS INTERMEDIATES

This invention relates to coumarin derivatives of formula (I)

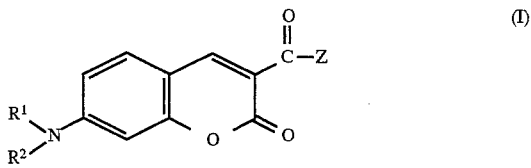

where $R^1$ and $R^2$ represent, independently of each other, hydrogen, $C_1$–$C_{30}$ alkyl, $C_6$–$C_{18}$ aryl or $C_7$–$C_{24}$ aralkyl, each of which may be substituted by hydroxy, amino, carboxy or $C_1$–$C_4$ alkoxycarbonyl, or $R^1$ and $R^2$, jointly with the nitrogen atom to which they are bonded, may represent a morpholine, piperidine, pyrrolidine or piperazine ring which may contain one or two substituents from the group comprising methyl, ethyl and phenyl, and Z represents an $OR^3$ group or

where $R^3$ represents $C_1$–$C_{30}$ alkyl, $C_6$–$C_{18}$ aryl $C_7$–$C_{24}$ aryl or $C_7$–$C_{24}$ aralkyl, which are each substituted by at least one hydroxy group, and wherein the aromatic rings may also be substituted in addition by halogen, $C_1$–$C_6$ alkyl or $C_1$–$C_6$ alkoxy, and $R^4$ and $R^5$, independently of each other, represent $C_1$–$C_{30}$ alkyl, $C_6$–$C_{18}$ aryl or $C_7$–$C_{24}$ aralkyl which are each optionally substituted by hydroxy, wherein at least one of the $R^4$ or $R^5$ radicals contains a hydroxy group and wherein the aromatic rings may also be substituted in addition by halogen, $C_1$–$C_6$ alkyl or $C_1$–$C_6$ alkoxy, wherein the aliphatic carbon chains, such as alkyl, alkoxy, alkylamino or aralkyl, for example, in $R^1$, $R^2$, $R^3$, $R^4$ and $R^5$ may be interrupted by one or more, preferably one or two, heteroatoms selected from oxygen, nitrogen and sulphur and/or by one or more, preferably one or two, phenylene rings which may be substituted by $C_1$–$C_4$ alkyl and/or by halogen.

The coumarin derivatives of formula (I) according to the invention contain at least one hydroxy group, via which they can be chemically bonded to polymer side chains.

The compounds according to the invention are therefore suitable for the production of polymers with luminophors on their side chains. Polymers such as these can be used in the light-emitting layer of a light-emitting diode.

$R^1$ and $R^2$ in formula (I) preferably represent, independently of each other, hydrogen or $C_1$–$C_{16}$ alkyl which is optionally substituted by hydroxy, amino, carboxy and/or $C_1$–$C_4$ alkoxycarbonyl, or phenyl, naphthyl, phenyl-$C_1$–$C_4$ alkyl or naphthyl-$C_1$–$C_4$ alkyl, each of which is unsubstituted or is substituted by $C_1$–$C_4$ alkyl, hydroxy, amino, carboxy, $C_1$–$C_4$ alkoxycarbonyl, chlorine and/or bromine.

In particular, $R^1$ and $R^2$ represent $C_1$–$C_{16}$ alkyl or phenyl which is optionally substituted by hydroxy, amino or phenyl.

Z in the aforementioned formula (I) represents $OR^3$ or $NR^4R^5$, where $R^3$ preferably represents $C_1$–$C_{16}$ alkyl, phenyl, naphthyl, phenyl-$C_1$–$C_4$ alkyl or naphthyl-$C_1$–$C_4$ alkyl, which are each substituted by at least one hydroxy group, and wherein the aromatic rings may also be substituted in addition by halogen, $C_1$–$C_6$ alkyl or $C_1$–$C_6$ alkoxy.

$R^4$ and $R^5$ preferably represent, independently of each other, $C_1$–$C_{16}$ alkyl, phenyl, naphthyl, phenyl-$C_1$–$C_4$ alkyl or naphthyl-$C_1$–$C_4$ alkyl, each of which is optionally substituted by hydroxy, wherein at least one of the $R^4$ and $R^5$ radicals contains a hydroxy group and the aromatic rings may also be substituted in addition by halogen, $C_1$–$C_6$ alkyl or $C_1$–$C_6$ alkoxy.

$R^3$ preferably represents $C_1$–$C_{12}$ alkyl which is substituted by hydroxy.

$R^4$ and $R^5$ most preferably represent, independently of each other, $C_1$–$C_{12}$ alkyl which is optionally substituted by hydroxy, wherein at least one of the $R^4$ and $R^5$ radicals contains a hydroxy group, wherein the aliphatic carbon chains, such as alkyl, alkoxy, alkylamino or aralkyl, for example, in $R^1$, $R^2$, $R^3$, $R^4$ and $R^5$ may be interrupted by one or more, preferably one or two, heteroatoms selected from oxygen, nitrogen and sulphur and/or by one or more, preferably one or two, phenylene rings which may be substituted by $C_1$–$C_4$ alkyl and/or by halogen.

This invention relates to a process for preparing coumarin derivatives of formula (I)

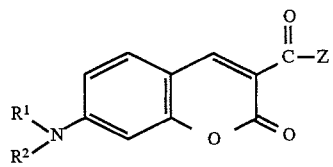

where $R^1$, $R^2$ and Z have the meaning given above, characterised in that a) when Z represents —$OR^3$, the malonic acid derivative of formula (IV)

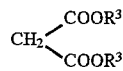

is prepared, preferably in a one-pot process, from the Meldrum's acid of formula (II)

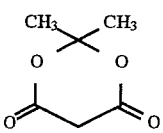

and an alcohol of formula (III)

optionally in the presence of a diluent, such as toluene, xylene or mesitylene, for example, under the catalysis of p-toluenesulphonic acid for example at temperatures in the range from 20° to 250° C., preferably 80° to 150° C., and that the malonic acid derivative of formula (IV) is subsequently reacted with a salicylaldehyde of formula (V)

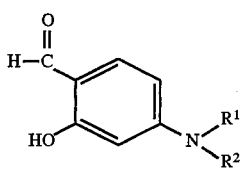

where $R^1$, $R^2$ and $R^3$ have the meanings given above, optionally in the presence of a diluent, such as toluene, xylene or mesitylene, for example, under the catalysis of piperidine acetate for example at temperatures in the range from 50° to 250° C., preferably 80° to 140° C., and b) when Z represents

a salicylaldehyde of formula (V) is reacted with a secondary amine of formula (VI) and a malonic acid derivative of formula (VII)

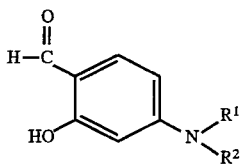

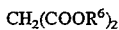

where $R^1$, $R^2$, $R^4$ and $R^5$ have the meanings given above, and $R^6$ represents a $C_1$–$C_6$ alkyl, optionally in the presence of a diluent, such as toluene, xylene or mesitylene, for example, under the catalysis of piperidine acetate for example at temperatures in the range from 50° to 250° C., preferably 80° to 140° C.

When carrying out method a) according to the invention, 1 mole of Meldrum's acid of formula (II), and 2–10 moles, preferably 3–6 moles of alcohol of formula (III) are generally used, and 0.5–1.0, preferably 0.9–1.0 moles of salicylaldehyde of formula (V) are generally used per mole of malonic acid derivative of formula (IV).

When carrying out method b) according to the invention, 2–20, preferably 5–10, moles of secondary amine and 1–2, preferably 1.2–1.5, moles of malonic acid derivative of formula (VII) are generally used per mole of salicylaldehyde of formula (V).

The preparation of the coumarin derivatives of formula (I) according to the invention when $Z=OR^3$ may be represented in the sense of a Knoevenagel condensation and subsequent cyclisation, for example, by the following reaction scheme:

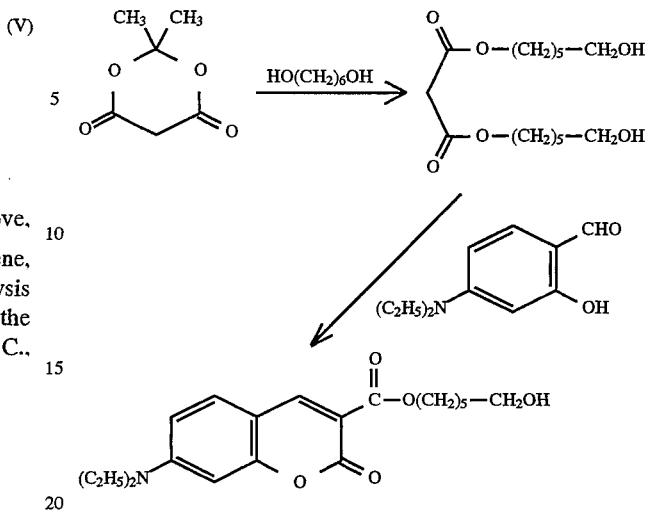

In the course of this procedure, bis-(6-hydroxyhexyl) malonate is first prepared by the reaction of the Meldrum's acid and 1,6-hexanediol, in the presence of catalytic amounts of p-toluenesulphonic acid, with the formation of acetone and water. The bis-(6-hydroxyhexyl) malonate is subsequently treated with 4-diethylamino-salicylaldehyde in the presence of catalytic amounts of piperidine acetate with the formation of the desired 3-(6-hydroxyhexoxycarbonyl)-7-diethylamino-coumarin.

The preparation of the coumarin derivatives of formula (I) according to the invention when $Z=NR^4R^5$ may be represented by the following reaction scheme, for example:

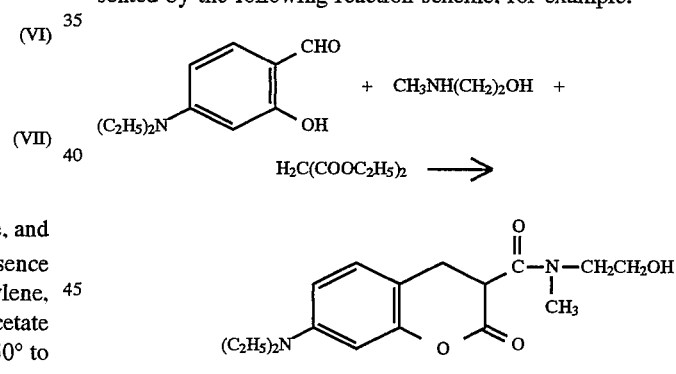

Here, 4-diethylamino-salicylaldehyde is reacted in the presence of catalytic amounts of piperidine acetate with diethyl malonate and 2-(methylamino)-ethanol. The desired 3-[(N-hydroxyethyl-N-methyl)aminocarbonyl]-7-diethylamino-coumarin is obtained.

The starting materials of formulae (II), (III), (IV), (V), (VI) and (VII) are compounds which are generally known in organic chemistry.

The compounds of formula (I) according to the invention are suitable for the production of (co)polymers with luminophors on their side chains, which are suitable for the construction of electroluminescent arrangements. The (co)polymers are synthesised from at least one recurring chain component of general formula (1) or (2) and optionally from recurring units of general formula (3)

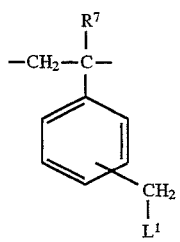 (1)

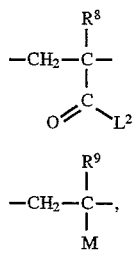 (2)

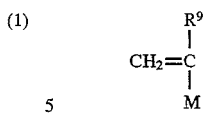 (1)

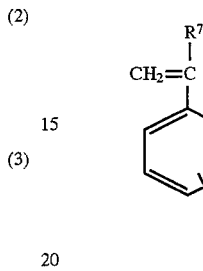 (6)

The monomers of formulae (4) and (5) are obtained from a coumarin derivative of formula (I) which is functionalised with at least one OH group, by reaction with a styrene or acrylic acid derivative of formulae (7) or (8).

 (7) (8)

(3)

where

R$^7$, R$^8$ and R$^9$, independently of each other, represent hydrogen or a C$_1$–C$_6$ alkyl, M represents CN or a C$_1$–C$_{30}$ alkoxycarbonyl, a C$_1$–C$_{30}$ (di)alkylaminocarbonyl or a C$_1$–C$_{30}$ alkylcarbonyl, which may each be substituted by hydroxy or by a C$_1$–C$_6$ alkoxycarbonyl, and further represents phenyl, naphthyl, anthracenyl, pyridyl or carbazolyl, which may each be substituted by radicals from the group comprising halogen, hydroxy, silyl, C$_1$–C$_{30}$ alkyl, C$_6$–C$_{18}$ aryl, C$_1$–C$_{30}$ alkoxy, C$_1$–C$_{30}$ alkoxycarbonyl, C$_1$–C$_{30}$ acyloxy and C$_1$–C$_{30}$ alkylcarbonyl, L$^1$ and L$^2$ represent, independently of each other, the derivatives of formula (I) described above, wherein bonding to the methylene group on the phenyl of monomer (1) or to the carbonyl group of monomer (2) via the oxygen of the OH group on the coumarin derivative is effected by the reaction of the OH group with a reactive group, e.g. a halogen (e.g. —CH$_2$Cl for monomer (1), —COCl for monomer (2)).

The proportion of structural units of formula (3) is 0 to 99.5, preferably 40 to 99.5 mole %, and the proportion of structural units (1) or (2) is 0.5 to 100, preferably 0.5 to 60 mole % in each case, wherein the molar proportions add up to 100%.

The (co)polymers described above can be produced by the usual polymerisation methods from the corresponding monomers of formulae (4) and (5), and optionally (6):

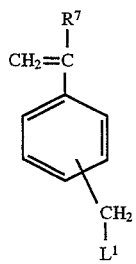 (4)

(5)

where

R$^{10}$ represents a halogen, preferably Cl or bromine, and

R$^{11}$ represents a halogen, preferably Cl or bromine, or hydroxy or a C$_1$–C$_4$ alkoxy, in the presence of a base such as triethylamine or pyridine or an alkali metal alcoholate at temperatures from –30° C. to 100° C., preferably 0° C. to 60° C.

The monomers of formula (6) are known or can be prepared by known methods.

The polymerisation processes are described in the literature. They may be effected ionically or radically. An anionic polymerisation can be initiated by an initiator such as butyllithium or lithium naphthalide, for example. A radical polymerisation can be initiated by radical initiators, such as azo initiators or peroxides for example, preferably AIBN (azoisobutyronitrile) or dibenzoyl peroxide. Production of the polymers can be effected free from solvent or in suitable solvents such as benzene, toluene, tetrahydrofuran, dioxane, ethyl acetate, xylene, chlorobenzene, 1-methoxy-2-propyl acetate, chlorinated hydrocarbons, acetone, etc., at temperatures of 20°–250° C.

The styrene and acrylic acid derivatives of formulas (7) and (8) and the monomers of formula (6) are compounds which are generally known.

The use of the coumarin derivatives of formula (I) according to the invention for the production of (co)polymers with luminophors on their side chains may be represented by the following reaction scheme, for example:

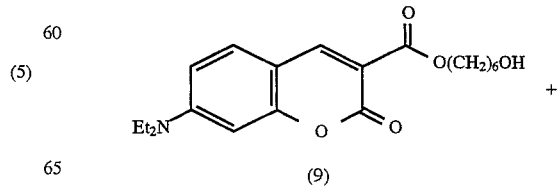

(9)

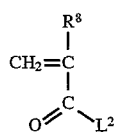

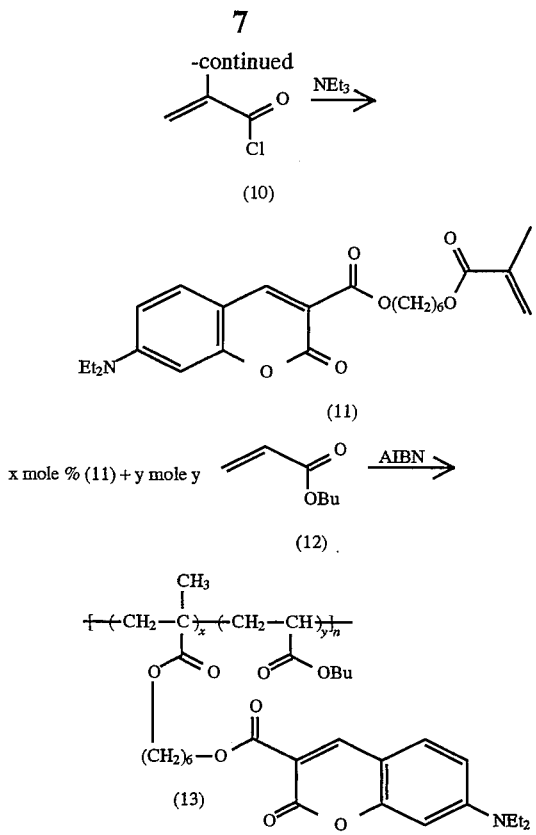

In the course of this procedure, methacrylate (11) is first prepared starting from 3-(6-hydroxyhexoxycarbonyl)-7-diethylamino-coumarin (9) and methacryloyl chloride (10) with the addition of triethylamine at 0° C. to room temperature. Methacrylate (11) can be polymerised in chlorobenzene at 100° C., in the presence of n-butyl acrylate (12) as the comonomer and with the addition of AIBN as a radical initiator, to form copolymer (13).

The (co)polymers have molecular weights ($\overline{M}_W$) within the range from 500 to 1 million g/mole, preferably 800 to 500,000 g/mole, determined by gel permeation chromatography. They are distinguished by their luminescent properties and film-forming capacities, and can be deposited on suitable substrates by casting, application by doctor blade or spin-coating. The products exhibit photoluminescence on irradiation, both in solution and as films. The (co)polymers are suitable for the construction of luminescent displays. These are characterised in that an electroluminescent layer is situated between two electrodes, that at least one of the two electrodes is transparent in the visible region of the spectrum, that light in the frequency range from 200 to 2000 nm is emitted when a DC voltage within the range from 0.1 to 100 volts is applied, that one or more intermediate layers may additionally be disposed between the electroluminescent layer and the electrodes.

These intermediate layers are known from the literature (see Appl. Phys. Lett., 57, 531 (1990)) and are described there as an HTL (hole transport layer) and as an ETL (electron transport layer). Amongst their other functions, the purpose of intermediate layers such as these is to increase the intensity of luminescence.

The electroluminescent polymers according to the invention may also be used in the electroluminescent layer as a mixture with each other or with at least one additional material. This additional material may comprise an inert binder, charge carrier transporting substances as described in EP-A 532 798 or EP-A 564 224, or mixtures of inert binders and charge carrier-transporting substances.

Amongst their other features, the mixtures of the polymers according to the invention and an additional material are further characterised in that they have film-forming properties and can be applied over a large surface to suitable substrates by casting, doctor blade application or spin-coating. Suitable substrates include transparent supports such as glass or plastics films (e.g. polyesters such as polyethylene terephthalate or polyethylene naphthalate, or polycarbonate, polysulphone or polyimide films).

The inert binder preferably comprises soluble, transparent polymers, such as polycarbonates, polystyrene, polyvinyl pyridine or polymethylphenyl siloxane, for example, and copolymers of polystyrene such as SAN, polysulphones, polyacrylates, polyvinyl carbazole, or vinyl acetate and vinyl alcohol polymers and copolymers.

EXAMPLES

Example 1

A solution of bis-(6-hydroxyhexyl) malonate in 1,6-hexanediol was reacted with a mixture comprising 21.6 g (0.15 mole) Meldmm's acid, 59 g (0.50 mole) 1,6-hexanediol and 0.28 g (1.5 mmole) p-toluenesulphonic acid monohydrate by heating for 2 hours at 140° C.

The resulting solution was subsequently treated with 26.0 g (0.135 mole) 4-diethylamino-salicylaldehyde, 0.7 ml piperidine and 0.1 ml acetic acid. The reaction mixture was stirred for 3 hours at 110° C., and was mixed with 300 ml water after cooling. The suspension was extracted with dichloromethane. The organic phase was concentrated and the residue was recrystallised from toluene.

40.2 g 3-(6-hydroxyhexoxycarbonyl)-7-diethylamino-coumarin (83% theoretical) were obtained as yellow crystals with a melting point of 85° to 86° C.

Example 2

A mixture of 19.3 g (0.10 mole) 4-diethylamino-salicylaldehyde and 19.2 g (0.12 mole) diethyl malonate was mixed with 30 ml 2-(methylamino)-ethanol, 0.3 ml piperidine and 0.3 ml acetic acid with stirring. The reaction mixture was stirred for 4 hours at 100° C. and was treated with 200 ml water after cooling. The suspension was extracted with dichloromethane. The organic phase was concentrated and the residue was recrystallised from toluene.

25.4 g 3-[(N-hydroxyethyl-N-methyl)-aminocarbonyl]-7-diethylamino-coumarin (80% theoretical) were obtained as brown crystals with a melting point of 94.5° to 96.5° C.

Example of use

1. Preparation of 3-(6-methacryloxyhexoxycarbonyl)-7-diethylamino-coumarin, formula (II) in the reaction scheme of Example 1.

8.36 g (0.08 mole) methacryloyl chloride (10) were added drop-wise with stirring, whilst cooling in iced water, to a solution of 16.3 g (0.045 mole) 3-(6-hydroxyhexoxycarbonyl)-7-diethylamino-coumarin (9) and 10.0 g (0.10 mole) of freshly distilled triethylamine in 50 ml of dry tetrahydrofuran. The reaction mixture was stirred for 5 hours at room temperature. The reaction mixture was subsequently treated with 200 ml water and 200 ml methylene chloride. After phase separation, the aqueous phase was extracted twice more, with 100 ml methylene chloride each time. The combined organic extracts were washed until neutral and dried over sodium sulphate. After distilling off the solvent in vacuum the residue was adsorptively filtered through a short silica gel column using diethyl ether as the mobile phase. 17.6 g of a pale yellow oil (92% theoretical) were obtained after distilling off the solvent.

2. Production of the copolymer according to formula (13) in the reaction scheme, with x=13 mole %, y=87 mole %.

A solution of 5.0 g (0.012 mole) 3-(6-methacryloxyhexoxycarbonyl)-7-diethylamino-coumarin (11), 10.0 g (0.078 mole) n-butyl acrylate (12) and 0.15 g (0.91 mmole) AIBN in 80 ml of dry chlorobenzene was degassed under vacuum and subsequently stirred for 3 hours under nitrogen at 100° C. The polymerisation mixture was then subsequently initiated using 0.15 g (0.91 mmole) AIBN added in three portions over 3 hours. The solution was then added drop-wise to 100 ml methanol with stirring, and the suspension was filtered off by suction. The crude product was precipitated twice more from a methylene chloride/methanol mixture. Yield: 12.7 g (85% theoretical).

2. Production of an electroluminescent arrangement

B glass coated with indium tin dioxide (ITO-coated glass, manufactured by Balzers) was cut into substrates of size 20×30 mm and cleaned. The following steps were performed in succession in the course of this procedure:

1) rinsing with distilled water and falterol for 15 minutes in an ultrasonic bath, 2) rinsing twice with fresh distilled water, for 15 minutes each time, in an ultrasonic bath, 3) rinsing with ethanol for 15 minutes in an ultrasonic bath, 4) rinsing twice with fresh acetone, for 15 minutes each time, in an ultrasonic bath, 5) drying on fluff-free lens cloths.

a 1% solution of the polymer according to formula (40) (Example 4) in 1,2-dichloroethane was filtered (0.2 µm filter, supplied by Sartorius). The filtered solution was distributed on the ITO glass using a centrifugal lacquer coating device at 1000 rpm. The thickness of the dry film was 110 nm and the Ra value [root mean square roughness value] of the surface was 5 nm (Alpha-Step 200 Stylus Profilometer supplied by Tencor Inst.)

The film produced in this manner was then vacuum-metallised to form Al electrodes. For this purpose, isolated Al spots with a diameter of 3 mm were evaporated on to the film by means of a perforated mask. During the vacuum metallising operation, the prevailing pressure in the vacuum-metallising apparatus (Leybold) was less than $10^{-5}$ mbar.

The ITO layer and the Al electrode were connected to a DC voltage source via an electrical supply. When the voltage was increased an electrical current flowed through the arrangement and the layer described above electroluminesced in the blue region of the spectrum.

We claim:
1. Coumarin derivatives of formula (I)

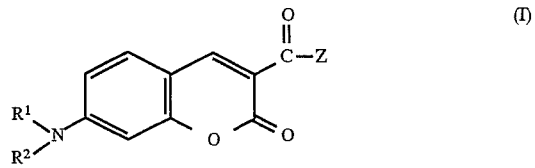

where $R^1$ and $R^2$ represent, independently of each other, hydrogen, $C_1$–$C_{30}$ alkyl, $C_6$–$C_{18}$ aryl or $C_7$–$C_{24}$ aralkyl, each of which may be substituted by hydroxy, amino, carboxy or $C_1$–$C_4$ alkoxycarbonyl, or $R^1$ and $R^2$, jointly with the nitrogen atom to which they are bonded, may represent a morpholine, piperidine, pyrrolidine or piperazine ring which may contain one or two substituents from the group comprising methyl, ethyl and phenyl, and Z represents an $OR^3$ group or

where $R^3$ represents $C_1$–$C_{30}$ alkyl, $C_6$–$C_{18}$ aryl or $C_7$–$C_{24}$ aralkyl, which are each substituted by at least one hydroxy group, and wherein the aromatic rings may also be substituted in addition by halogen, $C_1$–$C_6$ alkyl or $C_1$–$C_6$ alkoxy, and $R^4$ and $R^5$, independently of each other, represent $C_1$–$C_{30}$ alkyl, $C_6$–$C_{18}$ aryl or $C_7$–$C_{24}$ aralkyl which are each optionally substituted by hydroxy, wherein at least one of the $R^4$ or $R^5$ radicals contains a hydroxy group and wherein the aromatic rings may also be substituted in addition by halogen, $C_1$–$C_6$ alkyl or $C_1$–$C_6$ alkoxy, wherein the aliphatic carbon chains in $R^1$, $R^2$, $R^3$, $R^4$ and $R^5$ may be interrupted by one or more heteroatoms selected from oxygen, nitrogen and sulphur and/or by one or more phenylene rings which may be substituted by $C_1$–$C_4$ alkyl and/or by halogen.

2. Coumarin derivatives of formula (I) according to claim 1, wherein $R^1$ and $R^2$ represent, independently of each other, hydrogen or $C_1$–$C_{16}$ alkyl which is optionally substituted by hydroxy, amino, carboxy and/or $C_1$–$C_4$ alkoxycarbonyl, or phenyl, naphthyl, phenyl-$C_1$–$C_4$ alkyl or naphthyl-$C_1$–$C_4$ alkyl, each of which is unsubstituted or is substituted by $C_1$–$C_4$ alkyl, hydroxy, amino, carboxy, $C_1$–$C_4$ alkoxycarbonyl, chlorine and/or bromine, Z represents $OR^3$ or $NR^4R^5$, where $R^3$ represents $C_1$–$C_{16}$ alkyl, phenyl, naphthyl, phenyl-$C_1$–$C_4$ alkyl or naphthyl-$C_1$–$C_4$ alkyl, which are each substituted by at least one hydroxy group, and wherein the aromatic rings may also be substituted in addition by halogen, $C_1$–$C_6$ alkyl or $C_1$–$C_6$ alkoxy, $R^4$ and $R^5$ independently of each other, represent $C_1$–$C_{16}$ alkyl, phenyl, naphthyl, phenyl-$C_1$–$C_4$ alkyl or naphthyl-$C_1$–$C_4$ alkyl, each of which is optionally substituted by hydroxy, wherein at least one of the $R^4$ and $R^5$ radicals contains one hydroxy group and the aromatic rings may also be substituted in addition by halogen, $C_1$–$C_6$ alkyl or $C_1$–$C_6$ alkoxy, wherein the aliphatic carbon chains in $R^1$, $R^2$, $R^3$, $R^4$ and $R^5$ may be interrupted by one or more heteroatoms selected from oxygen, nitrogen and sulphur and/or by one or more phenylene rings which may be substituted by $C_1$–$C_4$ alkyl and/or by halogen.

3. Coumarin derivatives of formula (I) according to claim 1, characterised in that $R^1$ and $R^2$ represent $C_1$–$C_6$ alkyl or phenyl which are optionally substituted by hydroxy, amino or carboxy, or $R^1$ and $R^2$, jointly with the nitrogen atom to which they are bonded, represent a morpholine, piperidine, pyrrolidine or piperazine ring which may contain one or two substituents from the group comprising methyl, ethyl and phenyl, $R^3$ represents $C_1$–$C_{12}$ alkyl which is substituted by hydroxy, and $R^4$ and $R^5$, independently of each other, represent $C_1$–$C_{12}$ alkyl which is optionally substituted by hydroxy, wherein at least one of the $R^4$ and $R^5$ radicals contains a hydroxy group.

4. A method of preparing coumarin derivatives of formula (I) according to claim 1 wherein a) when Z represents —$OR^3$, the malonic acid derivative of formula (IV)

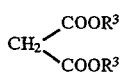  (IV)

is prepared from the Meldrum's acid of formula (II)

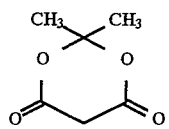  (II)

and an alcohol of formula (III)

$R^3$—OH  (III)

optionally in the presence of a diluent, under catalysis at temperatures within the range from 20° to 250° C., and that the malonic acid derivative of formula (IV) is subsequently reacted with a salicylaldehyde of formula (V)

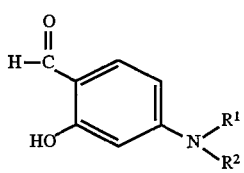  (V)

where $R^1$, $R^2$ and $R^3$ have the meanings given in claim 1, optionally in the presence of a diluent under catalysis at temperatures in the range from 50° to 250° C. and b) when Z represents

a salicylaldehyde of formula (V) is reacted with a secondary amine of formula (VI) and a malonic acid derivative of formula (VII)

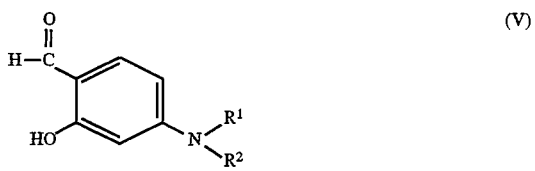  (V)

  (VI)

$CH_2(COOR^6)_2$  (VII)

where $R^1$, $R^2$, $R^4$ and $R^5$ have the meanings given above, and $R^6$ represents a $C_1$–$C_6$ alkyl, optionally in the presence of a diluent, at temperatures from 50° to 250° C.

5. The coumarin derivative of formula (I) according to claim 1 wherein $R^1$ and $R^2$ represent, independently, $C_1$–$C_{16}$ alkyl, or $R^1$ and $R^2$, jointly with the nitrogen atom to which they are bonded represents a morpholine, piperidine, pyrrolidine or piperazine ring, and Z represents $NR^4R^5$ wherein $R^4$ and $R^5$, independently of each other represent $C_1$–$C_{16}$ alkyl, each of which is optionally substituted by hydroxy, wherein at least one of the $R^4$ and $R^5$ radicals contain one hydroxy group and wherein the aliphatic carbon chain may be substituted by halogen.

6. The coumarin derivative of formula (I) according to claim 1 wherein $R^1$ and $R^2$ represent, independently $C_1$–$C_{16}$ alkyl, or $R^1$ and $R^2$, jointly with the nitrogen atom to which they are bonded, represents a morpholine, piperidine, pyrrolidine or piperazine ring, and Z is $OR^3$, wherein $R^3$ represents $C_1$–$C_{12}$ alkyl which is substituted by hydroxy.

7. A coumarin derivative comprising the compound 3-(6-hydroxyhexoxycarbonyl)-7-diethylamino-coumarin.

8. A coumarin derivative comprising the compound 3-[(N-hydroxyethyl-N-methyl)-aminocarbonyl]-7-diethylamino-coumarin.

9. A polymer having side chains containing the coumarin derivative as claimed in claim 1.

10. A polymer having side chains containing the coumarin derivative as claimed in claim 5.

11. A polymer having side chains containing the coumarin derivative as claimed in claim 6.

12. A polymer having side chains containing the coumarin derivative as claimed in claim 7.

* * * * *